United States Patent [19]

Jackson

[11] Patent Number: 4,751,294

[45] Date of Patent: Jun. 14, 1988

[54] SUCRALOSE CO-CRYSTALLIZED WITH A NITROGENOUS BASE

[75] Inventor: Graham Jackson, Reading, England

[73] Assignee: Tate & Lyle Public Limited Company, England

[21] Appl. No.: 818,720

[22] Filed: Jan. 14, 1986

[30] Foreign Application Priority Data

Jan. 14, 1985 [GB] United Kingdom ............... 8500862

[51] Int. Cl.$^4$ .................. C07H 3/04; C07H 5/02; C07H 15/00; A61K 9/68
[52] U.S. Cl. .................. 536/122; 536/18.5; 536/55.3; 514/23; 514/53; 514/355; 424/48; 424/49
[58] Field of Search ............. 536/18.5, 55.3, 122; 514/23, 53, 355; 424/48, 49

[56] References Cited

U.S. PATENT DOCUMENTS

| | | | |
|---|---|---|---|
| 3,478,015 | 11/1969 | Onishi et al. | 536/55.3 |
| 4,085,207 | 4/1978 | Aoki et al. | 514/23 |
| 4,343,934 | 8/1982 | Jenner et al. | 536/122 |

*Primary Examiner*—Ronald W. Griffin
*Assistant Examiner*—Nancy S. Carson
*Attorney, Agent, or Firm*—Ostrolenk, Faber, Gerb & Soffen

[57] ABSTRACT

Sucralose (4-chloro-4-deoxy-α-D-galactopyranosyl 1,6-dichloro-1,6-dideoxy-β-D-fructofuranoside) is thermally stabilized by co-crystallization with a nitrogenous base, for example niacinamide or an amino acid.

12 Claims, No Drawings

SUCRALOSE CO-CRYSTALLIZED WITH A NITROGENOUS BASE

This invention relates to preparations of chlorosucrose sweeteners of improved colour stability under hot, dry conditions.

Chlorosucrose sweeteners, i.e. compounds based on sucrose and galactosucrose in which one or more of certain hydroxy groups are replaced by chlorine atoms, are disclosed in British Pat. No. 1,543,167. Of particular interest is the compound sucralose, (4-chloro-4-deoxy-$\alpha$-D-galactopyranosyl 1,6-dichloro-1,6-dideoxy-$\beta$-D-fructo-furanoside, otherwise known as 4,1',6'-trichloro-4,1',6'-trideoxygalactosucrose). Chlorosugars of this type are intensely sweet (having a sweetness several hundred times that of sucrose) and are of particular interest as low calorie sweeteners to replace saccharin. They are in general relatively stable and inert: a feature that is particularly marked in acid aqueous solutions, in complete contrast to peptide-based sweeteners.

It has been found that, in contrast to the situation under dissolved conditions, under completely dry conditions, discoloration of the crystalline sweetener can be a problem at high ambient temperatures. For example, if apparently pure dry sucralose is maintained at 100° C., the colour has changed after a period of 20 minutes from colourless (white) to pale brown.

It has now found that it is possible to stabilize a chlorosucrose sweetener such as sucralose against thermal discoloration by actually co-crystallizing the sweetener with a minor proportion of a nitrogenous base so that the crystalline product contains, for example, about 0.03 to 3.0% by weight of the base. Simply mixing the sucralose with such buffering substances does not provide the necessary protection. The problem, however, with any of the bases which might possibly be of use in the present invention is that they must be capable of providing the desired effect at the level at which they can be induced to co-crystallise with sucralose from a suitable solvent. Furthermore, this level must be reproducible.

The nitrogenous base is preferably an amine. Effective amines include secondary or tertiary amines which may either be aliphatic or, preferably cyclic, e.g. imidazole, pyridazine and morpholine.

One preferable class of bases comprises the amino acids. These naturally occurring compounds are accepted as dietary compounds and are themselves either harmless or positively beneficial. It is difficult to generalise on this, as some amino acids are much more useful than others. However, it appears to be the case that the acid ones, such as L-glutamic acid, L-cystine and L-aspartic acid are of little use. Basic amino acids such as L-histidine are not much better, although L-lysine alkali metal salts are highly effective and cyclic compounds, such as L-tryptophan and its alkali metal salts, are quite effective. Of the simple amino acids (one amine, one acid), the alkali metal salts of glycine and alanine are of marked interest and L-methionine is also of use. The alkali metal salts of amides such as L-asparagine are of especial interest. Finally, cyclic forms such as L-proline and L-hyroxyproline and their alkali metal salts provide a pronounced effect.

In general, the better compounds provide a crystalline sucralose containing 0.2 to 3% of amino acid and provide several hours protection against discolouration of dry sucralose at 100° C.

However, it is of particular importance that the nitrogenous base shoul be an accepted food additive, and it is particularly advantageous that the most effective nitrogenous base that we have so far found is in fact niacinamide, otherwise known as 3-pyridine carboxylic acid amide, and generally classed as a B vitamin. Niacinamide is, of course, both a tertiary amine and an amide. It has the ability to be co-crystallized easily with sucralose without adversely affecting the crystals. In particular, it has the advantage of having a suitable solubility in an ester solvent such as ethyl acetate, which is preferred for the final crystallization of sucralose. Thus, if a solution of sucralose in ethyl acetate is augmented with 1 to 10% by weight (based on the sucralose) of niacinamide, the sucralose can be crystallized from the solution, washed with further ethyl acetate and dried under vacuum to give a fine crystalline material containing about 0.3-0.9% of niacinamide in the sucralose. Such a material has a much improved colour stability compared with normal sucralose and, for example, under the test conditions described above, would be practically unchanged after 7 or more hours at 100° C.

Niacinamide has further advantages over some other amines and amides, of being both tasteless and odourless and of being completely safe and non-toxic, at the extremely low levels at which it is incorporated in the sucralose. It can also be crystallised with sucralose at a reproducible level. As the sucralose itself need only be incorporated in an oral product at very low levels, for example about 0.015% by weight, the actual content of the niacinamide in the final sweetened product would only range from about, say, 0.5 to 1.5 ppm.

The sweetness of sucralose was not affected by incorporation of niacinamide at 0.58%.

The following examples illustrate the invention.

EXAMPLE 1

The additives were incorporated into sucralose by crystallising sucralose from an ethyl acetate solution containing the additive, except in the case of sodium acetate where ethanol was used as the crystallizing solvent. It is necessary to do this, because simple dry-mixing of sucralose and the additive is not effective in enhancing stability. The procedure for incorporating niacinamide is detailed below.

To a solution of sucralose (10 g) in methanol (50 ml) was added niacinamide (0.5 g). The solution was evaporated with vacuum at 50° to give a residue which was re-dissolved in ethyl acetate, the evaporation was repeated to ensure the removal of methanol, and the residue was then redissolved in ethyl acetate (50 ml). This solution was cooled to 20° and allowed to crystallize overnight with stirring. The crystals of sucralose were filtered off, washed with ethyl acetate (25 ml) and dried. This gave a level of incorporation of niacinamide of 0.79%.

Similar crystallizations were effected with other bases in similar amounts, to give a product containing the base in the quantity indicated in Tables 3, 4 and 5 below. Each of the crystalline materials was then subjected to the stated temperatures in an open vessel and the time taken for a pale brown colour to develop was noted.

The results are given in the following Tables 1-5.

TABLE 1

Incorporation of niacinamide into sucralose

| SAMPLE NO. | AMOUNT OF NIACINAMIDE ADDED (mg/g sucralose) | % NIACINAMIDE IN SAMPLE[a] |
|---|---|---|
| A1 | 10 | 0.29 |
| A2 | 10 | 0.38 |
| B1 | 20 | 0.50 |
| B2 | 20 | 0.45 |
| C1 | 50 | 0.79 |
| C2 | 50 | 0.77 |
| D1 | 80 | 0.85 |
| D2 | 80 | 0.85 |
| E1 | 100 | 0.63 |
| E2 | 100 | 0.66 |

TABLE 2

Colour Stability of sucralose with and without Niacinamide at 50°, 70° and 100° C.

| SAMPLE NO. | % NIA-CINAMIDE | APPROX. TIME FOR SAMPLE TO BECOME VERY PALE BROWN | | |
|---|---|---|---|---|
| | | 100° | 70° | 50° |
| Control | 0.0 | 20 mins | 12 hrs | 9 days |
| A1 | 0.29 | 1.5 hrs | 5 days | 5 weeks |
| A2 | 0.38 | 3 hrs | 6 days | 12 weeks |
| B1 | 0.50 | 4 hrs | 10 days | 20 weeks |
| B2 | 0.45 | 4 hrs | 10 days | 20 weeks |
| E1 | 0.63 | 6.5 hrs | 13 days | 30 weeks |
| E2 | 0.66 | 5.5 hrs | 10 days | 30 weeks |
| C1 | 0.79 | 5.5 hrs | 14 days | >20 weeks |
| C2 | 0.77 | >7 hrs | 16 days | >30 weeks |
| D1 | 0.85 | >7 hrs | 16 days | >30 weeks |
| D2 | 0.85 | >7 hrs | 16 days | >30 weeks |

TABLE 3

Incorporation of Bases Into sucralose

| BASE | % BASE IN SAMPLE[a] | TIME (MINUTES) FOR SAMPLE TO BECOME VERY PALE BROWN AT 100° C. |
|---|---|---|
| Control | 0.0 | 20 |
| Imidazole | 0.32 | 40 |
| Morpholine | 0.3 | 150 |
| Pyridazine | 0.03 | 90 |
| Sodium acetate | 0.02 | 50 |

TABLE 4

Incorporation of L-amino acids into sucralose

| AMINO ACID | % AMINO ACID INCORPORATED | APPROX. TIME (MINUTES) FOR SAMPLE TO BECOME VERY PALE BROWN AT 100° C. |
|---|---|---|
| L-arginine | 0.52 | 40 |
| L-tyrosine | 0.26 | 27 |
| L-histidine | 1.30 | 77 |
| glycine | 0.43 | 105 |
| L-glutamic acid | 0.42 | 45 |
| L-hydroxyproline | 1.03 | >280 |
| L-valine | 1.50 | 65 |
| L-proline | 1.31 | >280 |
| L-glutamine | 0.10 | 30 |
| L-asparagine 2H$_2$O | 0.80 | 55 |
| L-cystine | — | 32 |
| L-tryptophan | 2.19 | 130 |
| L-leucine | 1.87 | 45 |
| L-isoleucine | 2.15 | 25 |
| L-phenylalanine | 2.00 | 80 |
| L-serine | 0.45 | 80 |
| L-alanine | 0.95 | 35 |
| L-methionine | 1.92 | 120 |
| L-aspartic acid | — | 30 |
| Control | 0.0 | 20 |

[a]This figure is an estimate based on nitrogen analysis.

TABLE 5

Incorporation of sodium salts of L-amino acids into sucralose

| AMINO ACID SODIUM SALT | % AMINO ACID INCORPORATED | APPROX. TIME (MINUTES) FOR SAMPLE TO BECOME VERY PALE BROWN AT 100° C. |
|---|---|---|
| Glycine | 1.04 | 280 |
| L-histidine | 1.90 | 105 |
| L-hydroxy-proline | 1.31 | >140 |
| L-proline | 0.29 | >140 |
| L-lysine | 0.54 | >280 |
| L-aspartic acid (di-Na) | 1.77 | 40 |
| L-aspargine | 2.86 | >280 |
| L-serine | 0.82 | 40 |
| L-tryptophan | 0.97 | 115 |
| L-valine | 0.69 | 40 |
| L-cystine (mono-Na) | 2.15 | 75 |
| L-alanine | 0.48 | 135 |
| L-methionine | <0.24 | 103 |
| L-phenylalanine | <0.13 | 60 |
| L-glutamic acid (di-Na) | 1.91 | 95 |
| L-glutamine | 0.60 | 70 |
| L-isoleucine | 0.33 | 60 |
| Control | 0.0 | 20 |

[a]This figure is an estimate based on nitrogen analysis.

EXAMPLE 2

Larger scale production

The method for incorporation of niacinamide into sucralose crystals was repeated on a larger scale as follows.

To a solution of sucralose (10 kg) in methanol (50 liters) was added niacinamide (0.5 kg). The solution was evaporated with vacuum at 50° C. to give a residue which was re-dissolved in ethyl acetate and the evaporation repeated to ensure the removal of methanol. The residue was then re-dissolved in ethyl acetate (50 liters), the solution cooled to 20° C. and mixed with a high shear mixer for 1 hour to nucleate the crystallisation. The slurry was then stirred for 16 hours and the crystals of sucralose were filtered off, washed into ethyl acetate (25 liters) and dried. The level of incorporation of niacinamide was found to be 0.43%. A yield of 7.5 kg of product was obtained.

The colour-stability of the product was greater than 4 months at 50° C. when measured by the procedures described in Example 1.

I claim:

1. Sucralose (4-chloro-4-deoxy-α-D-galactopyranosyl 1,6-dichloro-1,6-dideoxy-β-D-fructofuranoside) co-crystallized with an up to 100° C. color stabilizing amount of an acceptable food additive, co-crystallizable nitrogenous base.

2. Sucralose according to claim 1 co-crystallized with an aliphatic or cyclic secondary or tertiary amine.

3. Sucralose according to claim 1 co-crystallised with an amino acid.

4. Sucralose according to claim 2, co-crystallised with a cyclic tertiary amine which has an amide group.

5. Sucralose according to claim 4, co-crystallised with niacinamide.

6. Sucralose according to claim 5 containing 0.3 to 0.9% by weight of niacinamide.

7. A method of improving the color stability up to 100° C. of sucralose by crystallizing it from a co-solution of sucralose and an acceptable food additive, co-crystallizable nitrogenous base to obtain a co-crystallized product containing sucralose and a color stabilizing amount of said base.

8. A method according to claim 7, in which the base is an aliphatic or cyclic secondary or tertiary amine.

9. A method according to claim 7, in which the base is an amino acid.

10. A method according to claim 8, in which the base is a cyclic tertiary amine which has an amide group.

11. A method according to claim 10, in which the base is niacinamide.

12. A method according to claim 11 in which the product contains 0.3 to 0.9% by weight of niacinamide.

* * * * *